United States Patent [19]

Arai et al.

[11] Patent Number: 5,130,401
[45] Date of Patent: Jul. 14, 1992

[54] ROOM TEMPERATURE CURABLE ORGANOPOLYSILOXANE COMPOSITION HAVING GOOD ADHESIVE PROPERTIES, PARTICULARLY FOR CHLORINATED POLYETHYLENE

[75] Inventors: Masatoshi Arai, Annaka; Kouji Yokoo, Tomioka; Yoshifumi Harada, Haruna, all of Japan

[73] Assignee: Shin-Etsu Chemical Co., Ltd., Tokyo, Japan

[21] Appl. No.: 639,337

[22] Filed: Jan. 10, 1991

[30] Foreign Application Priority Data

Jan. 12, 1990 [JP] Japan ........................ 2-5770

[51] Int. Cl.$^5$ ............................. C08G 77/04
[52] U.S. Cl. ........................ 528/33; 528/34; 528/38; 528/41
[58] Field of Search ................ 528/33, 34, 38, 41

[56] References Cited

U.S. PATENT DOCUMENTS

| | | |
|---|---|---|
| 3,635,887 | 1/1972 | Polmanteer .................. 528/41 |
| 3,839,246 | 10/1974 | Hamilton, Jr. et al. ........... 528/34 |
| 4,039,503 | 8/1977 | Itoh ............................. 528/34 |
| 4,460,739 | 7/1984 | Ashby ......................... 528/34 |
| 4,697,026 | 9/1987 | Lee et al. ..................... 528/41 |
| 4,826,915 | 5/1989 | Stein et al. ................... 528/34 |

*Primary Examiner*—John C. Bleutge
*Assistant Examiner*—Margaret W. Glass
*Attorney, Agent, or Firm*—Oblon, Spivak, McClelland, Maier & Neustadt

[57] ABSTRACT

The room temperature curable organopolysiloxane composition comprises a silane compound having a group represented by the following formula:

$$-\text{NHCHCH}_2\text{COO}-$$
$$\phantom{-\text{NHCH}}|$$
$$\phantom{-\text{NHCH}}R$$

wherein R is a hydrogen atom or a monovalent hydrocarbon group, as an adhesion assistant. The composition has the merit of good adhesive properties, particularly for chlorinated polyethylene.

6 Claims, 1 Drawing Sheet

ROOM TEMPERATURE CURABLE ORGANOPOLYSILOXANE COMPOSITION HAVING GOOD ADHESIVE PROPERTIES, PARTICULARLY FOR CHLORINATED POLYETHYLENE

BACKGROUND OF THE INVENTION

1. Field of the Invention

This invention relates to a room temperature curable organopolysiloxane composition which shows good adhesive properties, particularly for chlorinated polyethylene.

2. Description of the Prior Art

Room temperature curable organopolysiloxane compositions are widely used for adhesion or fixing of various electric and electronic parts, because of their good properties. The conventional room temperature curable organopolysiloxane compositions generally comprise an aminosilane as an adhesion assistant, and have good adhesive properties for many adherends.

On the other hand, flame-retardant chlorinated polyethylene has recently has come to be widely used as a portion of an electric or electronic part or the like.

However, the conventionally known room temperature curable organopolysiloxane compositions do not show any adhesive properties for the chlorinated polyethylene.

SUMMARY OF THE INVENTION

Accordingly, it is an object of this invention to provide a room temperature curable organopolysiloxane composition which shows good adhesive properties, particularly for chlorinated polyethylene.

This invention is based on the success in enhancing remarkably the adhesive properties of a room temperature curable organopolysiloxane composition for chlorinated polyethylene by use of an organosilicon compound having a group represented by the following general formula [I]:

wherein R represents a hydrogen atom or a monovalent hydrocarbon group, as an adhesion assistant.

Thus, according to this invention, there is provided a room temperature curable organopolysiloxane composition comprising:

(A) a diorganopolysiloxane having at least two terminuses each of which has a hydroxyl group, 2 or 3 alkoxy groups or 2 or 3 vinyloxy groups;

(B) a filler;

(C) an organosilicon compound having at least 3 hydrolyzable groups in one molecule thereof and/or a partially hydrolyzed product of the organosilicon compound;

(D) a curing catalyst; and (E) an organosilicon compound having a group represented by the following general formula [I]:

wherein R represents a hydrogen atom or a monovalent hydrocarbon group of from 1 to 8 carbon atoms.

The room temperature curable composition of this invention has remarkably high adhesive properties for chlorinated polyethylene, and is useful as an adhesive for electric and electronic parts, especially those parts in which chlorinated polyethylene is used. The composition of this invention, naturally, is also excellent in adhesive properties for a variety of substrates other than chlorinated polyethylene, and in other properties. Therefore, the room temperature curable composition is also effective for use as sealing agent, caulking agent, coating agent, water repellent, mold release agent, fiber treating agent, etc. for various substrates.

DETAILED DESCRIPTION OF THE INVENTION

(A) Diorganopolysiloxane

Figure 1:
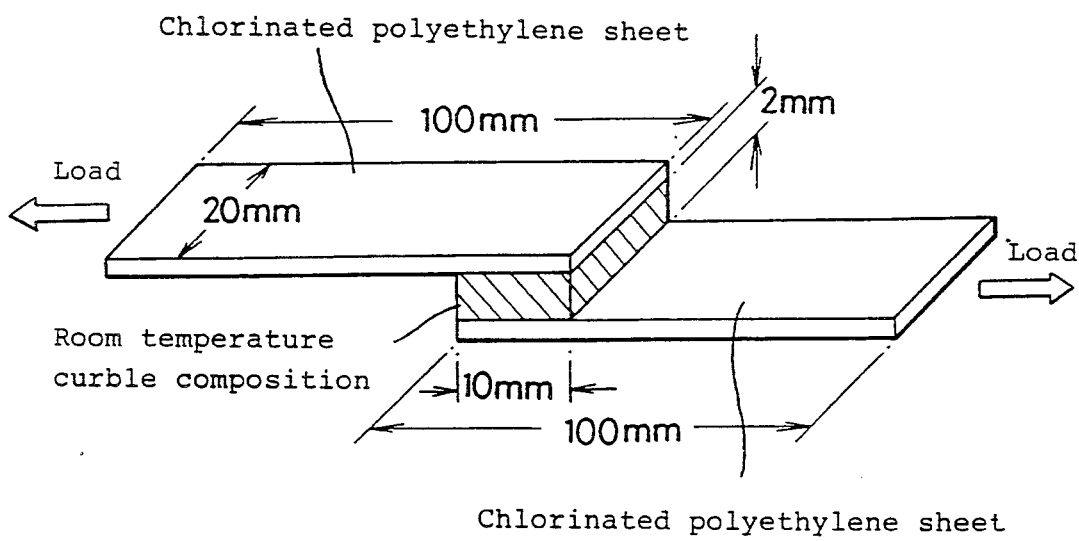
FIG. 1 illustrates the structure of a test piece for a shear adhesion test used in Examples which will be described hereinbelow.

In the composition according to this invention, the diorganopolysiloxane of component (A) serves as a main constituent of the composition, and is one which is represented by, for example, the following average composition formula:

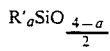

wherein the groups R' are each independently a substituted or unsubstituted monovalent hydrocarbon group, and a is a number of from 1.90 to 2.05, and which has at least two terminuses each of which has a hydroxyl group, 2 to 3 alkoxy groups or 2 or 3 vinyloxy groups in its molecule.

Examples of the groups R' in the above general formula include alkyl groups such as methyl, ethyl, propyl, butyl, 2-ethylbutyl, octyl, etc.; cycloalkyl groups such as cyclohexyl, cyclopentyl, etc.; alkenyl groups such as vinyl, allyl, butenyl, hexenyl, etc.; aryl groups such as phenyl, tolyl, xylyl, naphtyl, diphenyl, etc.; aralkyl groups such as benzyl, phenylethyl, etc.; substituted hydrocarbon groups corresponding to these groups in which some or all of the carbon-bonded hydrogen atoms are replaced by halogen atom, cyano group or the like, such as chloromethyl, trifluoropropyl, 2-cyanoethyl, 3-cyanopropyl, etc.; and so on. Of these groups, preferred are those having 1 to 10 carbon atoms, particularly 1 to 6 carbon atoms.

As the alkoxy group at the end of the molecular chain, there can be included, for example, methoxy, ethoxy, propoxy, butoxy, methoxyethoxy, ethoxyethoxy, etc.

Besides, the diorganopolysiloxane of component (A) is essentially a straight-chain one, but may contain a branched structure in part.

Further, in order that a cured product obtained from the composition of this invention may have good rubber elasticity and mechanical strength, it is preferable for the diorganopolysiloxane to have a viscosity at 25° C. of from 25 to 500,000 cSt, preferably from 100 to 100,000 cSt.

(B) Filler

In the composition of this invention, the filler used as component (B) may be one which is well known per se. For example, particulate silica, silica aerogel, precipitated silica, diatomaceous earth, metallic oxides such as iron oxide, zinc oxide, titanium oxide, etc., or those obtained by treating the surfaces of these materials with a silane; metallic carbonates such as calcium carbonate, magnesium carbonate, zinc carbonate, etc.; powdered synthetic resins such as polystyrene, polyvinyl chloride, polypropylene, etc.; and asbestos, glass wool, carbon black, particulate mica, fused silica, etc.

At least one of these fillers may be used either singly or in combination. Furthermore, it is preferable that the filler is used in an amount of from 1 to 400 parts by weight, particularly from 5 to 200 parts by weight, per 100 parts by weight of the organopolysiloxane (A). If the amount of the filler is less than 1 part by weight, a cured product of the resulting composition tends to be poor in mechanical strength. When the amount of the filler is more than 400 parts by weight, on the other hand, the resulting composition will have an increased viscosity with lowered workability, and a cured product of the composition may be so low in rubber strength that the intended rubber elastic product cannot be obtained.

(C) Organosilicon Compound Having Hydrolyzable Group

As component (C) of the composition according to this invention, an organosilicon compound having at least 3 hydrolyzable groups in its molecule or a partially hydrolyzed product of the organosilicon compound is used. This component is an essential ingredient for curing the composition at room temperature in the presence of moisture.

The hydrolyzable groups include, for example, alkoxy groups such as methoxy, ethoxy, propoxy, butoxy, methoxyethoxy, ethoxyethoxy, etc.; acyloxy groups such as acetoxy, propionoxy, butyloyloxy, benzoyloxy, etc.; alkenyloxy groups such as isopropenyloxy, isobutenyloxy, 1-ethyl-2-methylvinyloxy, etc.; iminoxy groups such as dimethyl ketoxime group, methyl ethyl ketoxime group, diethyl ketoxime group, cyclopentanoxime group, cyclohexanoxime group, etc.; amino groups such as N-metylamino, N-ethylamino, N-propylamino, N-butylamino, N,N-dimethylamino, N,N-diethylamino, cyclohexylamino, etc.; amido groups such as N-methylacetamido, N-ethylacetamido, N-methylbenzamido, etc.; aminoxy groups such as N,N-dimethylaminoxy, N,N-diethylaminoxy, etc.; and so on.

Exemplary organosilicon compounds for use as component (C) having such hydrolyzable groups as above include alkoxysilanes such as methyltrimethoxysilane, vinyltriethoxysilane, 3-chloropropyltrimethoxysilane, 3-aminopropyltriethoxysilane, etc.; ketoximesilanes such as methyltris(dimethyl oxime)silane, methyltris(-methyl ethyl ketoxime)silane, tetra(methyl ethyl ketoime)silane, etc.; acyloxysilanes such as vinyltriacetoxy-silane, methyltriacetoxysilane, etc.; alkenyloxysilanes such as vinyltripropenyloxysilane, methyl-triisobutenyloxysilane, etc.; amidosilanes such as phenyltris(N-methylacetamido)silane, vinyltris(N-ethylacetamido)silane, etc.; aminosilanes such as vinyltris(N-butylamino)silane, phenyltris(N,N-diethylamino)silane, etc.; aminoxysilanes such as methyltris(N,N-dimethylaminoxy)silane, vinyltris(N,N-diethylaminoxy)silane, etc.; and partially hydrolyzed products of these silanes. At least one of these organosilicon compounds may be used either singly or in combination.

The amount of the organosilicon compounds or partially hydrolyzed products thereof to be used as component (C) is preferably from 0.5 to 50 parts by weight, particularly from 1 to 10 parts by weight, per 100 parts by weight of the organopolysiloxane (A). If the amount of component (C) used is less than 0.5 part by weight, effective curing of the composition cannot be achieved, whereas the use of component (C) in an amount of more than 50 parts by weight is liable to worsen the properties of the cured elastic product obtained or to be disadvantageous on an economical basis.

(D) Curing catalyst

As the curing catalyst of component (D), there can be used those various curing catalysts which have conventionally been used in this type of compositions, for example, metallic salts of organic carboxylic acid such as lead 2-ethyloctoate, dibutyltin diacetate, dibutyltin dilaurate, butyltin 2-ethylhexoate, iron 2-ethylhexoate, cobalt 2-ethylhexoate, manganese 2-ethylhexoate, zinc 2-ethylhexoate, stannous caprylate, tin naphthenate, tin oleate, tin butyrate, titanium naphthenate, zinc naphthenate, cobalt naphthenate, zinc stearate, etc.; organic titanates such as tetrabutyl titanate, tetra-2-ethylhexyl titanate, triethanolamine titanate, tetra(isopropyloxy) titanate, etc.; organotitanium compounds such as organosiloxytitanium, β-carbonyltitanium, etc.; alkoxyaluminium compounds, aminoalkyl-substituted alkoxysilanes such as 3-aminopropyltriethoxysilane, N-(trimethoxysilylpropyl)ethylenediamine, etc.; amine compounds and salts thereof, such as hexylamine, dodecylamine phosphate, etc.; quaternary ammonium salts such as benxylethylammonium acetate, etc.; lower fatty acid salts of alkali metals, such as potassium acetate, sodium acetate, lithium oxalate, etc.; dialkylhydroxylamines such as dimethylhydroxylamine, diethylhydroxylamine, etc.; guanidine compounds and guanidyl-containing silane or siloxane, represented by the following formulas:

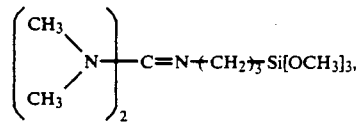

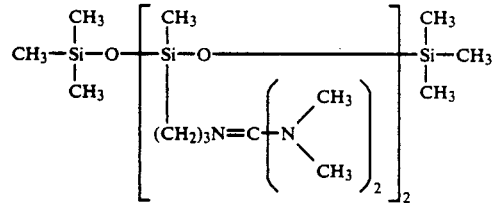

and so on. At least one such curing catalyst may be used either singly or in combination.

The curing catalyst of component (D) as mentioned above is preferably used in an amount of generally from 0.01 to 10 parts by weight, particularly from 0.1 to 3 parts by weight, per 100 parts by weight of the organopolysiloxane (A), though the amount varies depending on the kind of the aforementioned component (C). If the amount of component (D) is below the range, it takes long for the resultant composition to be cured, and, particularly where the intended cured product of the composition is thick, it is likely to be difficult for the composition to be cured uniformly to a deep portion thereof. If the amount of component (C) is above the range, on the other hand, the time required for forming a coat of the composition is extremely short. In that case, various inconveniences are generated on a workability basis, and the cured product obtained is liable to be poor in properties such as heat resistance, weatherability, etc.

(E) Organosilicon Compound Containing Specified Organic Group

In this invention, it is important to use an organosilicon compound containing an organic group represented by the aforementioned formula[I]:

—NHCHRCH$_2$COO—  [I]

wherein R is as defined above. The organosilicon compound serves as an adhesion assistant, and incorporation of the organosilicon compound in the room temperature curable organopolysiloxane composition enhances greatly the adhesive properties of the composition, particularly for chlorinated polyethylene.

In the above formula [I], R represents a hydrogen atom or a monovalent hydrocarbon group of up to 8 carbon atoms, as mentioned above. Examples of the monovalent hydrocarbon group include alkyl groups such as methyl, ethyl, propyl, butyl, etc. and phenyl. Of these monovalent hydrocarbon groups, preferred are those having from 1 to 6 carbon atoms.

The organosilicon compounds as described above include, for example, silane compounds represented by the following general formula [II] or [III]:

$Y_3Si—R^1—Z—R^1—SiY_3$  [II]

$Y_3Si—R^1—Z—R^2$  [III]

wherein Z is a group represented by the above general formula [I],
Y is an alkoxyl group,
R$^1$ is an alkylene group, and
R$^2$ is an alkyl group.

Here, the alkoxy group Y may be, for example, methoxy, ethoxy, propoxy, butoxy, methoxyethoxy, ethoxyethoxy, etc., in which the methoxy and ethoxy groups are preferred. As the alkylene group R$^1$, for example, those having from 1 to 6 carbon atoms can be used, with the trimethylene group being preferred. The alkyl group R$^2$ may be, for example, methyl, ethyl, propyl, butyl, etc., with the ethyl group being preferred.

The preferred examples of the organosilicon compound as described above include the following silane compounds:

(1) (EtO)$_3$SiC$_3$H$_6$NHCH$_2$CH$_2$COOC$_3$H$_6$Si(OMe)$_3$, (2) (MeO)$_3$SiC$_3$H$_6$NHCH$_2$CH$_2$COOC$_3$H$_6$Si(OMe)$_3$, (3) (MeO)$_3$SiC$_3$H$_6$NHCH$_2$CH$_2$NHCH$_2$CH$_2$COOC$_3$H$_6$Si(OEt)$_3$,

(5) (EtO)$_3$SiCH$_2$NHCH$_2$CH$_2$COOC$_3$H$_6$Si(OMe)$_3$,

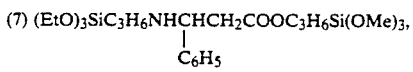

(8) (MeO)$_3$SiC$_3$H$_6$NHCH$_2$CH$_2$NHCH$_2$CH$_2$COOC$_3$H$_6$Si(OMe)$_3$, (9) (EtO)$_3$SiC$_3$H$_6$NHCH$_2$CH$_2$COOEt, and

(10) EtNHCH$_2$CH$_2$COOC$_3$H$_6$Si(OMe)$_3$, wherein Me is the methyl group and Et is the ethyl group, and the same meanings apply hereinbelow.

Among the above silane compounds, those in which two trialkoxysilane skeletons are linked to each other through an organic group having a group represented by the aforementioned formula [I] show a remarkable enhancing effect on the adhesive properties.

The organosilicon compounds as above can be obtained easily by reacting an aminosilane or organic amine having a primary amino group with an organosilicon compound or organic compound having an organic group represented by the general formula: RCH=CH—COO— (where R is as defined above) under heating. One exemplar of the reaction is represented by the following formula:

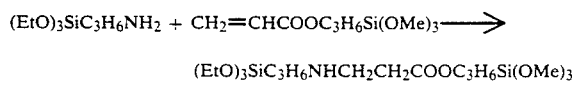

It is preferable that the organosilicon compound of component (E) is incorporated in an amount of generally from 0.01 to 10 parts by weight, particularly from 0.1 to parts by weight, per 100 parts by weight of the organopolysiloxane (A). If the amount of component (E) is less than 0.01 parts by weight, the enhancing effect on the adhesive properties of the organopolysiloxane composition for chlorinated polyethylene is not displayed effectively. When the amount is more than 10 parts by weight, on the other hand, a cured product of the organopolysiloxane composition obtained may show lowered properties.

Other Ingredients

The composition of this invention comprising the aforementioned components (A) to (E) as essential constituents can, if necessary, further comprise various additives such as thixotropy-imparting agent, coloring agents such as inorganic pigments and organic dyes, age resistor, antioxidant, antistatic agent, heat conductivity improving agent, etc. according to the intended use of the composition. Furthermore, in order to enhance the workability in using the composition, a diluent such as hydrocarbon solvent, etc. may also be used.

Room Temperature Curable Composition

The composition of this invention can be obtained easily by mixing uniformly the aforementioned components and, optionally, other ingredients. The mixing is carried out under shielding from moisture, at a temperature preferably ranging from room temperature to 100° C.

The composition according to the invention is easily cured at room temperature in the presence of moisture in air, to form a rubber elastic cured product.

EXAMPLES

In the following examples, the term "part(s)" means "part(s) by weight", without exception.

EXAMPLE 1

To 100 parts of dimethylpolysiloxane having a viscosity of 20,000 cSt at 25° C. and blocked by the hydroxyl group at its molecular end, 12 parts of fumed silica having surfaces treated with trimethylsilyl groups was added, followed by mixing uniformly to prepare a base compound.

Next, 112 parts of the base compound was admixed with 7.84 parts of vinyltributanoximesilane, 0.22 part of dibutyltin dioctoate and 1.12 parts of a silane having the following structure:

(MeO)$_3$SiC$_3$H$_6$NHCH$_2$CH$_2$COOC$_3$H$_6$Si(OMe)$_3$, and the admixture was mixed uniformly to prepare a room curable composition.

The composition was then sandwiched between two 2-mm thick sheets of chlorinated polyethylene (produced by Showa Denko K. K.) to prepare a test piece for shearing test, as shown in FIG. 1. After curing for 7 days under the conditions of 20° C. and 55% RH, the test piece was subjected to measurement of adhesive strength under shear, to give an adhesive strength value of 11 kgf/cm$^2$.

EXAMPLES 2 TO 6, COMPARATIVE EXAMPLES 1 TO 3

Room curable compositions were prepared in the same manner as in Example 1 except that various silane compounds were used in place of the silane compound used in Example 1 as component (E), and shear adhesion tests were carried out in the same manner as in Example 1. The silane compounds used and the measured values of adhesive strength under shear are shown in Table 1.

TABLE 1

| | Organosilicon compound (component E) | Adhesive strength under shear |
|---|---|---|
| Example 1 | (MeO)$_3$SiC$_3$H$_6$NHCH$_2$CH$_2$COOC$_3$H$_6$Si(OMe)$_3$ | 11 |
| Example 2 | (EtO)$_3$SiC$_3$H$_6$NHCH$_2$CH$_2$COOC$_3$H$_6$Si(OMe)$_3$ | 13 |
| Example 3 | (MeO)$_3$SiC$_3$H$_6$NHCH$_2$CH$_2$NHCH$_2$CH$_2$COOC$_3$H$_6$Si(OMe)$_3$ | 11 |
| Example 4 | (EtO)$_3$SiC$_3$H$_6$NHCHCH$_2$COOC$_3$H$_6$Si(OMe)$_3$<br>                                                 \|<br>                                              CH$_3$ | 11 |
| Example 5 | (EtO)$_3$SiC$_3$H$_6$NHCH$_2$CH$_2$COOEt | 7 |
| Example 6 | EtNHCH$_2$CH$_2$COOC$_3$H$_6$Si(OMe)$_3$ | 6 |
| Comparative Example 1 | (EtO)$_3$SiC$_3$H$_6$NH$_2$ | 0.5 |
| Comparative Example 2 | (MeO)$_3$SiC$_3$H$_6$NHCH$_2$CH$_2$NH$_2$ | 0.3 |
| Comparative Example 3 | (MeO)$_3$SiC$_3$H$_6$NH$_2$ | 0.3 |

Note: The values of adhesive strength under shear are in kgf/cm$^2$.

EXAMPLE 7

To 100 parts of dimethylpolysiloxane having a viscosity of 20,000 cSt at 25° C. and blocked by the trimethoxysilyl group at its molecular end, 18 parts of fumed silica having surfaces treated with trimethylsilyl groups was added, followed by mixing with heating at 180° C. for 4 hours to prepare a base compound.

Next, 118 parts of the base compound was admixed with 2.36 parts of (MeO)$_3$SiCH$_2$COOEt, 0.24 part of dibutyltin dimethoxide, 0.59 part of 1,1,3,3-tetraguanidylpropyltrimethoxysilane and 1.18 parts of a silane having the following structure:

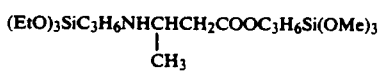
(EtO)$_3$SiC$_3$H$_6$NHCHCH$_2$COOC$_3$H$_6$Si(OMe)$_3$
                                |
                                CH$_3$ and the admixture was mixed uniformly, to prepare a room temperature curable composition.

The adhesive strength under shear of the composition was determined, in the same manner as in Example 1, to be 18 kgf/cm$^2$.

We claim:
1. A room temperature curable organopolysiloxane composition comprising:
   (A) a diorganopolysiloxane having at least two terminuses each of which has a hydroxyl group, 2 or 3 alkoxy groups or 2 or 3 vinyloxy groups;
   (B) a filler;
   (C) an organosilicon compound having at least 3 hydrolyzable groups in one molecular thereof and/or a partially hydrolyzed product of the organosilicon compound;
   (D) a curing catalyst; and
   (E) a silane compound represented by the following general formula [II]:

$$Y_3-Si-R^1-Z-R^1-SiY_3 \quad [II]$$

wherein Z is a group represented by the following general formula [I]:

$$-NHCHRCH_2COO- \quad [I]$$

wherein R represents a hydrogen atom or a monovalent hydrocarbon group of up to 8 carbon atoms,
Y is an alkoxyl group, and
R$^1$ is an alkylene group.

2. The composition according to claim 1, which comprises from 1 to 400 parts by weight of the filler (B), from 0.5 to 50 parts by weight of the organosilicon compound (C), from 0.01 to 10 parts by weight of the curing catalyst (D) and from 0.01 to 10 parts by weight of the organosilicon compound (E) per 100 parts by weight of the organopolysiloxane (A).

3. The composition according to claim 1, comprising an organosilicon compound represented by the above general formula [I] in which the monovalent hydrocarbon group R is an alkyl group or phenyl group as the organosilicon compound (E).

4. The composition according to claim 1, wherein the organosilicon compound (E) is a silane compound selected from the group consisting of:
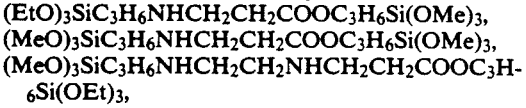
(EtO)$_3$SiC$_3$H$_6$NHCH$_2$CH$_2$COOC$_3$H$_6$Si(OMe)$_3$,
(MeO)$_3$SiC$_3$H$_6$NHCH$_2$CH$_2$COOC$_3$H$_6$Si(OMe)$_3$,
(MeO)$_3$SiC$_3$H$_6$NHCH$_2$CH$_2$NHCH$_2$CH$_2$COOC$_3$H$_6$Si(OEt)$_3$,

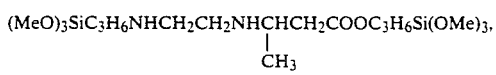

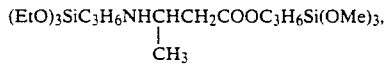

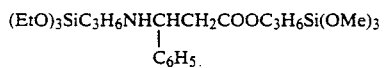

and
(MeO)$_3$SiC$_3$H$_6$NHCH$_2$CH$_2$NHCH$_2$CH$_2$COOC$_3$H$_6$Si(OMe)$_3$, wherein Me is the methyl group and Et is the ethyl group.

5. The composition according to claim 1, wherein the organosilicon compound (C) is at least one selected from the group consisting of alkoxysilane, ketoximesilane, acyloxysilane, alkenyloxysilane, amidosilane, aminosilane, aminoxysilane and partially hydrolyzed products of these silanes.

6. A cured product obtained by curing the composition as claimed in claim 1.

* * * * *